United States Patent
Duffy

(10) Patent No.: US 6,902,057 B2
(45) Date of Patent: Jun. 7, 2005

(54) PACKAGING DEVICE FOR A CATHETER ASSEMBLY

(75) Inventor: Niall Duffy, Galway (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 67 days.

(21) Appl. No.: 10/350,894

(22) Filed: Jan. 24, 2003

(65) Prior Publication Data

US 2004/0144667 A1 Jul. 29, 2004

(51) Int. Cl.$^7$ .............................................. B65D 83/10
(52) U.S. Cl. ...................................... 206/364; 206/438
(58) Field of Search .............................. 206/63.3, 303, 206/363, 364, 438

(56) References Cited

U.S. PATENT DOCUMENTS

| | | | | |
|---|---|---|---|---|
| 3,851,649 A | * | 12/1974 | Villari | 206/438 |
| 4,085,845 A | * | 4/1978 | Perfect | 206/564 |
| 4,216,860 A | | 8/1980 | Heimann | |
| 5,031,768 A | * | 7/1991 | Fischer | 206/370 |
| 5,284,244 A | * | 2/1994 | O'Toole et al. | 206/363 |
| 5,339,955 A | * | 8/1994 | Horan et al. | 206/370 |
| 5,353,929 A | * | 10/1994 | Foster | 206/364 |
| 5,441,152 A | * | 8/1995 | Estes | 206/570 |
| 5,947,284 A | * | 9/1999 | Foster | 206/364 |
| 6,047,815 A | * | 4/2000 | Cerwin et al. | 206/63.3 |
| 6,557,704 B1 | * | 5/2003 | Randolph | 206/363 |
| 2002/0130059 A1 | | 9/2002 | Armijo | |

FOREIGN PATENT DOCUMENTS

| | | |
|---|---|---|
| EP | 0782868 A1 | 7/1997 |
| EP | 0820781 A1 | 1/1998 |

* cited by examiner

Primary Examiner—John A. Ricci

(57) ABSTRACT

The present invention protects a catheter during shipment and storage. The device holds a portion of the catheter suspended such that the portion does not contact the device. When the suspended portion includes a stent treated with a therapeutic coating, the coating is protected from physical damage and from the risk that extended contact of the coating with packaging materials may result in the therapeutic agent migrating out of the coating and into the packaging materials or components of the packaging materials migrating into the therapeutic coating, both of which can occur if a therapeutic coating remains in contact with another material for an extended period of time. A catheter bearing an untreated stent, a balloon catheter, and other types of catheter would be similarly protected from physical or chemical damage.

35 Claims, 4 Drawing Sheets

PACKAGING DEVICE FOR A CATHETER ASSEMBLY

TECHNICAL FIELD

This invention relates generally to packaging and storage containers for medical catheters. More specifically, the invention relates to a packaging device designed to protect a catheter assembly bearing a stent during shipping and storage.

BACKGROUND OF THE INVENTION

Heart disease, specifically coronary artery disease, is a major cause of death, disability, and healthcare expense in the United States and other industrialized countries. In atherosclerosis, one form of heart disease, deposits of hard plaques (atheromas) may be formed within the inner coat of a vessel (intima) and inner media of arteries. This atherosclerotic disease process leads to a critical narrowing (stenosis) of the affected coronary artery and produces anginal syndromes, known commonly as chest pain. The progression of the narrowing reduces blood flow, triggering the formation of a blood clot (thrombus). The clot may further reduce or entirely prevent the flow of oxygen-rich blood to heart muscles, causing a heart attack. Alternatively, the clot may break off and lodge in the vessel of another organ, such as the brain, resulting in a thrombotic stroke.

One method for treating atherosclerosis and other forms of coronary narrowing is percutaneous transluminal coronary angioplasty (PTCA). During PTCA, commonly, a balloon catheter device is inflated within the stenotic vessel. Upon inflation, the pressurized balloon exerts a compressive force on the lesion, thereby increasing the inner diameter of the affected vessel.

Soon after the procedure, however, a significant proportion of treated vessels restenose. To prevent restenosis, a stent may be implanted within the vessel. The stent acts as a scaffold to support the lumen in an open position and maintain lumen size. For insertion, the stent is affixed in a compressed configuration along the delivery catheter, for example, crimped onto a balloon that is folded or otherwise wrapped about a guide wire. After the stent is properly positioned within the vessel, it is expanded, causing the length of the stent to contract and the diameter to expand.

Because stent insertion can cause undesirable reactions such as inflammation, infection, thrombosis, or proliferation of cell growth that occludes the passageway, stents are sometimes coated with therapeutic agents to assist in preventing these conditions. The coatings are bioengineered to release precise doses of the therapeutic agent. However, if the coating remains in direct contact with another material for an extended period of time, for example, during shipping and storage, the therapeutic agent may migrate into the other material, resulting in delivery of a lower dose of the therapeutic agent than intended. Alternatively, components of the other material may migrate into the therapeutic coating, again leading to impaired performance of the therapeutic agent.

Uncoated stents that have undergone chemical or other treatments may also be at risk of damage from contact with packaging material. The treated stent may be damaged not only by extended contact, but also by brief contact that results in scratching, as might occur when a protective sleeve is dragged across the surface of a stent.

Therefore, it would be desirable to have an improved packaging device for protecting a stent affixed to a distal portion of a catheter system that overcomes the aforementioned and other disadvantages.

SUMMARY OF THE INVENTION

One aspect of the present invention is a catheter packaging device having a base portion and a catheter-holding portion. The base portion includes a bottom surface, a perimeter wall, and at least one retaining member extending inward from the perimeter wall. The catheter-holding portion includes a protective Well and at least one support member. A distal portion of a catheter is suspended within the protective well when the catheter is held by at least one support member. The catheter packaging device may also have a luer-holding portion. The device may further have a removable covering means that encloses at least a portion of the catheter packaging device.

Another aspect of the present invention is a method of protecting a catheter within a catheter packaging device. A first distal portion of the catheter is retained within at least one support member. A second distal portion of the catheter is retained within at least one support member. A third distal portion of the catheter is suspended such that the third distal portion does not contact the catheter packaging device. A first proximal portion of the catheter is retained in a coiled configuration within the catheter packaging device. A second proximal portion of the catheter is retained in a fixed position within the catheter packaging device.

A further aspect of the present invention is a system for protecting a catheter within a catheter packaging device. The system comprises means for retaining a first distal portion of the catheter within at least one support member, retaining a second distal portion of the catheter within at least one support member, suspending a third distal portion of the catheter such that the third distal portion does not contact the catheter packaging device, retaining a first proximal portion of the catheter in a coiled configuration within the catheter packaging device, and retaining a second proximal portion of the catheter in a fixed position within the catheter packaging device.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 2:
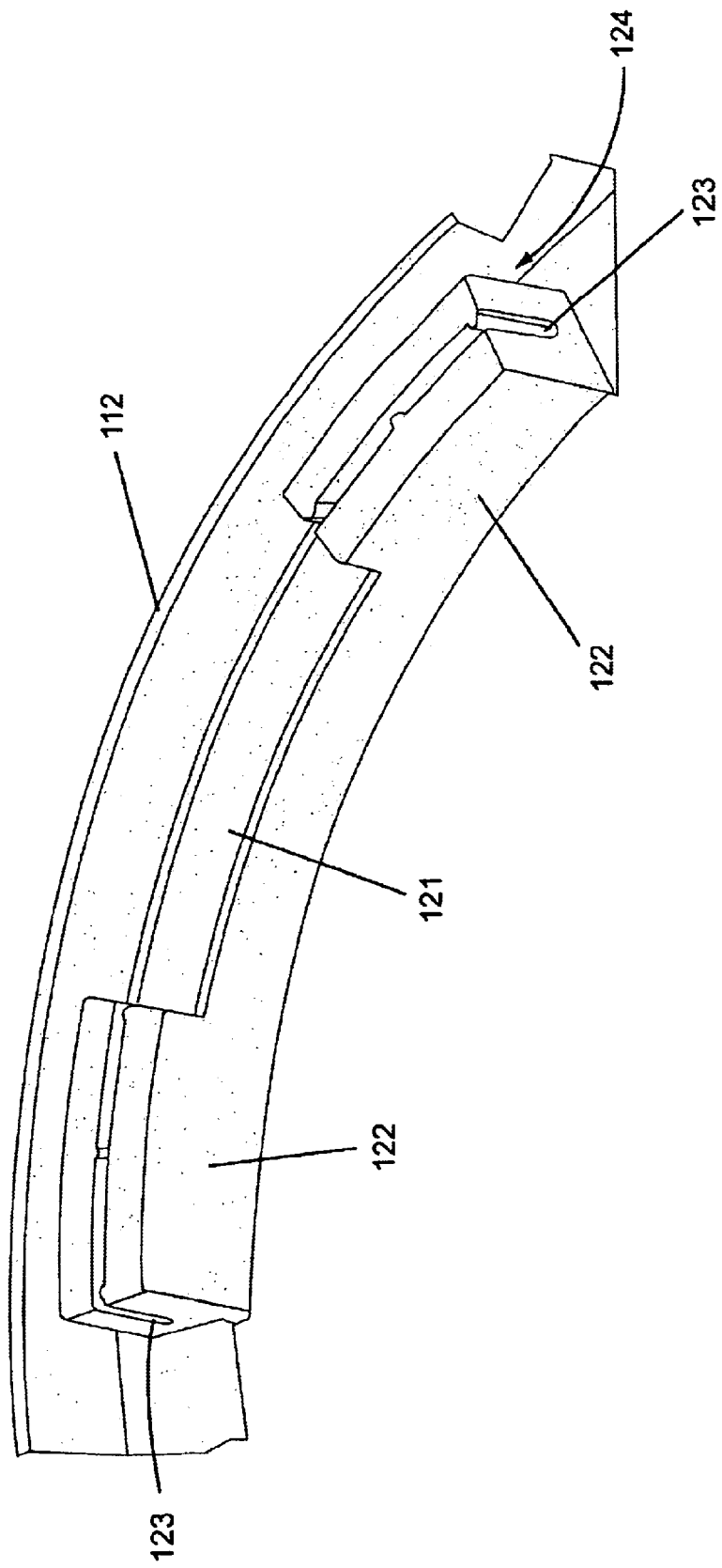
FIG. 2 is an enlarged, fragmentary view of a catheter-holding portion of a catheter packaging device according to FIG. 1.
Figure 3:
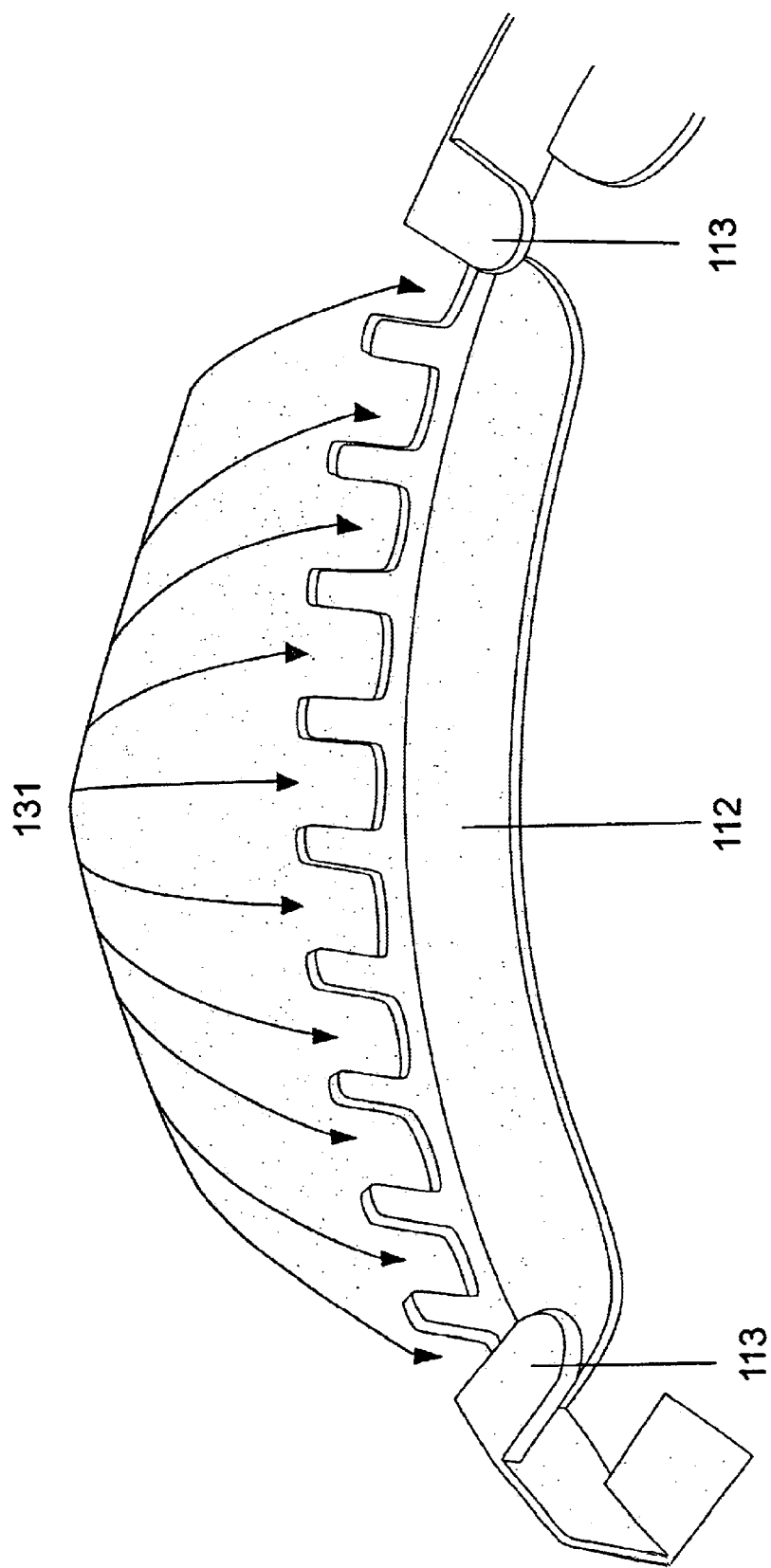
FIG. 3 is an enlarged, fragmentary view of a luer-holding portion of a catheter packaging device according to FIG. 1.

One aspect of the present invention is a catheter packaging device. One embodiment of the device, in accordance with the present invention, is illustrated in FIG. 1 at 100 and in enlarged, fragmentary views in FIG. 2 and FIG. 3.

Device 100 may include a base portion 110, a catheter-holding portion 120, and a luer-holding portion 130. Base portion 110 may include a bottom surface 111, a perimeter wall 112, at least one retaining member 113, and a recess 114 for finger access to a stored catheter. Catheter holding portion 120 may include a protective well 121 and at least one support member 122. Support member 122 may include an elongate channel 123. A channel 124 may be provided between the catheter-holding portion 120 and the perimeter wall to contain a portion of a coiled catheter. Luer-holding portion 130 may include at least one opening 131 into which a wing section or side arm of a luer may be placed.

Figure 1:
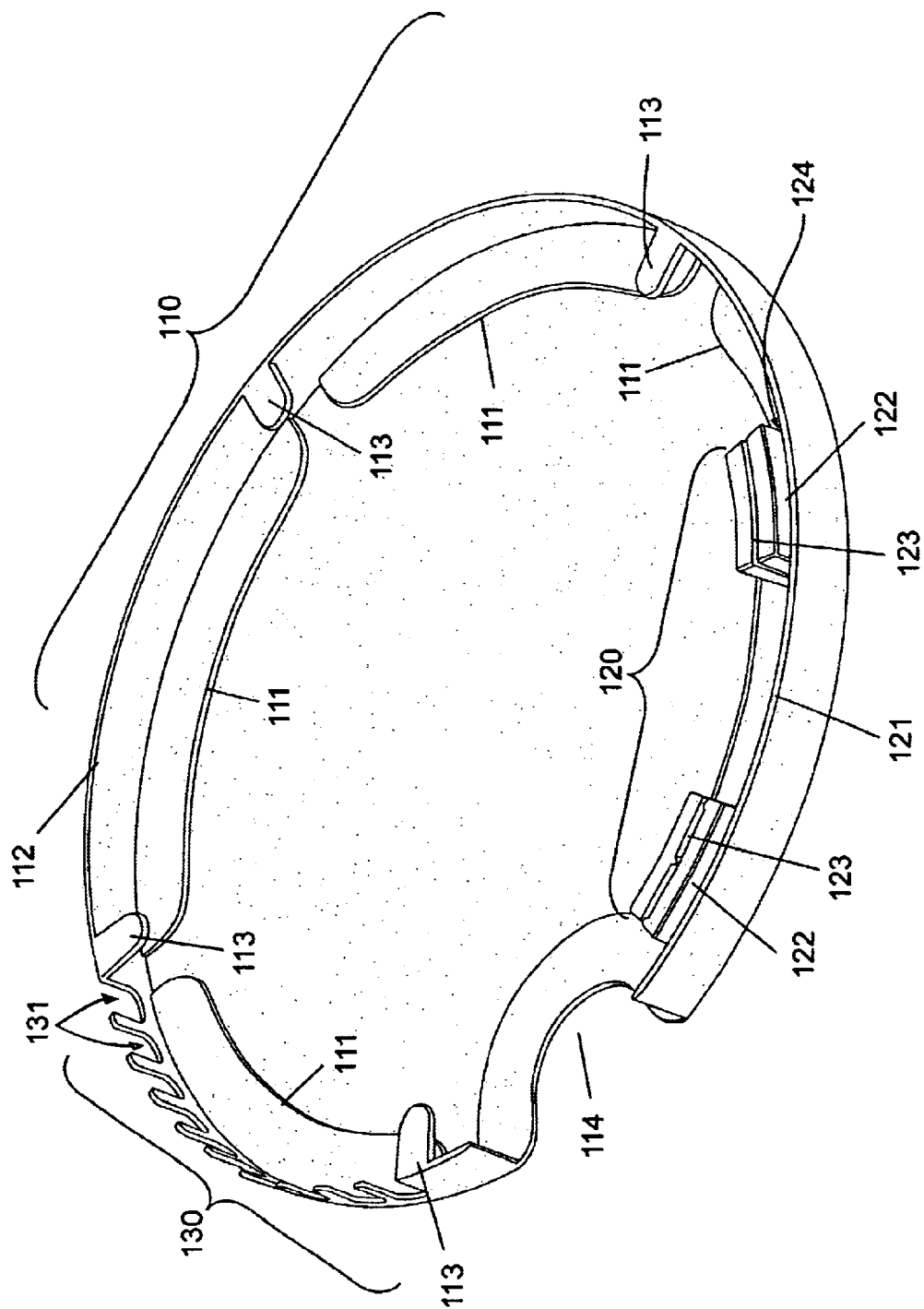
FIG. 1 is an illustration of one embodiment of a catheter packaging device, in accordance with the present invention.

Device 100 and its base portion 110 may be ringlike, as shown in FIG. 1. The device also may be any other shape capable of retaining a catheter without inducing kinks or other undesirable deformations in the catheter.

The bottom surface 111 of base portion 110 may comprise, for example, multiple narrow sections as shown in FIG. 1. It also may comprise a single ringlike structure, a structure that covers the entire base of the device, or any appropriate structure capable of supporting and retaining a coiled catheter.

Perimeter wall 112 may be oriented perpendicular to the bottom surface of the catheter packaging device. It may surround all or a portion of the bottom surface 111.

Retaining members 113 may be, for example, tabs that extend inward from the upper edge of the perimeter wall to prevent a coiled catheter from springing out of the device. The number and dimensions of the retaining members may be selected to ensure a catheter is held securely within the device during shipment and storage but may be easily and safely removed for use.

A recess 114 may be formed in the bottom surface and perimeter wall of the catheter packaging device to further facilitate removal of a coiled catheter from the packaging device.

Catheter-holding portion 120 may be integrally formed into the bottom surface of the catheter packaging device, or it may be fabricated separately and secured to the device using any appropriate means known in the art. Catheter-holding portion 120 is shown in an enlarged, fragmentary view in FIG. 2, in which like elements share like reference numbers with FIG. 1.

Protective well 121 may comprise a recessed area within the catheter-holding portion 120 that is sized to suspend a distal portion of a catheter within the well. The catheter portion, for example a portion bearing a treated stent, is protected by being held suspended in air such that it does not contact the catheter packaging device.

Individual support members 122 may extend distally and proximally from the protective well 121. Alternatively, a single support member may at least partially enclose and extend beyond the protective well.

Each support member 122 may include an elongate channel 123 into which a portion of the catheter may be placed. For example, a catheter tip or a stylet may be placed into the distal support member, and a portion of the catheter that is proximal to a balloon or treated stent may be placed into the proximal support member. The elongate channel 123 may include a plurality of protrusions that extend into the channel from each side to releasably grip a portion of the catheter. Alternatively, the elongate channel 123 may comprise a material that provides a high coefficient of friction between the channel and the catheter, allowing the, catheter portion to be releasably held within the channel by friction. The elongate channel 123 may be arcuate.

While channeled support members are shown in FIG. 1, those skilled in the art will appreciate that many other means for releasably holding the catheter are possible. For example, the support members may include a clip, or a removable covering means may assist in holding the catheter in place.

Catheter packaging device 100 may include a narrow passageway or channel 124 between perimeter wall 112 and catheter-holding portion 120. As the catheter is coiled into the device, a proximal portion of the catheter may be placed into this channel.

The luer-holding portion 130 of the device may include at least one opening 131 within the perimeter wall that is positioned to hold a wing section or side arm of a luer. A plurality of openings 131 may allow the same packaging device to be used for catheters of various lengths. The luer-holding portion 130 is shown in an enlarged, fragmentary view in FIG. 3, in which like elements share like reference numbers with FIG. 1.

Catheter packaging device 100 may be fabricated from any suitable material that can be conventionally formed and processed, for example polypropylene, polyethylene, a nylon/polyethylene blend, or polytetrafluoroethylene (PTFE). Such materials may minimize exchange of chemical components between the catheter system and the device during shipment and storage. That is, such materials may be nonreactive with a therapeutic agent carried in a stent coating or with other desirable coating materials, thus reducing or eliminating the risk of a therapeutic agent or other coating component migrating out of the coating and into the device material, or of a component of the device material migrating into the therapeutic agent or other coating material. Device 100 may be fabricated using one or more methods such as blow molding or injection molding.

Catheter packaging device 100 may also include a removable covering means, for example a lid that encloses at least a portion of the catheter packaging device. The lid may be transparent, allowing the contained device to be readily identified without opening or removing the packaging. The lid may include at least one accessory-holding portion shaped to hold items such as instructions for use or flushing cannulae during shipment and storage. Use of a covering means that encloses or seals the packaging device may eliminate the need for any additional packaging such as cardboard boxes or storage bags.

The described embodiment is designed to be used in conjunction with a catheter bearing a treated stent, for example a stent that has undergone coating, chemical treatment, or any other desired treatment. However, it is anticipated that the present invention may be used to protect a catheter bearing an untreated stent, a balloon catheter, or any type of catheter requiring protection.

Figure 4:
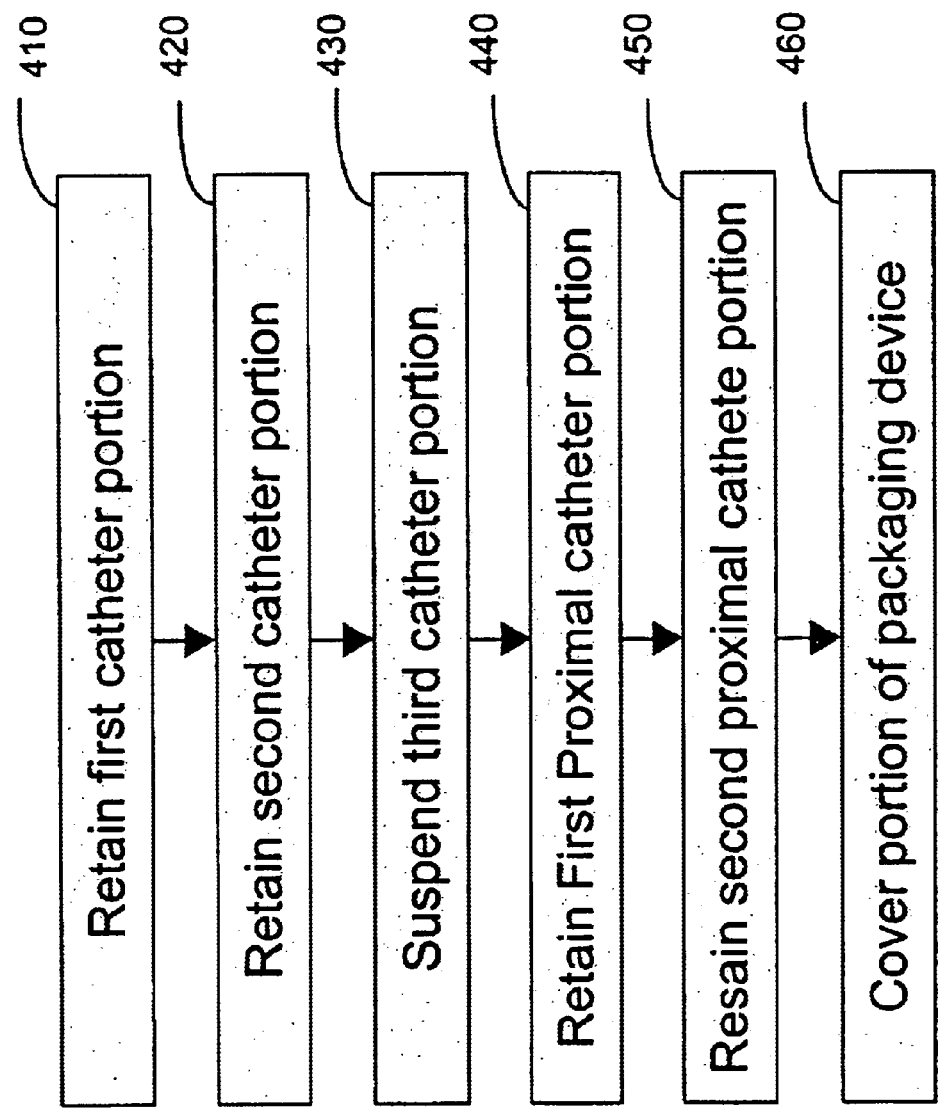
FIG. 4 is a flow diagram of one embodiment of a method for protecting a catheter within a catheter packaging device in an example device according to FIG. 1.

Another aspect of the present invention is a method of protecting a catheter within a catheter packaging device. FIG. 4 shows a flow diagram of one embodiment of a method in accordance with the present invention at 400.

A catheter tip or stylet is placed into and retained by a first support member (Block 410). A second portion of the catheter, for example a portion adjacent and proximal to a treated stent, is placed into and retained by a second support member (Block 420). The catheter portion between the tip or stylet and the second retained portion is thereby suspended between the two support members such that it does not contact the catheter packaging device and is protected from damage during shipment and storage (Block 430).

A proximal portion of the catheter is then coiled within the catheter packaging device (Block 440) and held in place by tabs that prevent the catheter from springing out of the device. A wing section or side arm of the luer is placed into an opening in the perimeter wall (Block 450), securing the proximal end of the catheter within the device. A lid or cover may then be placed over the packaging device (Block 460).

In practice, the present invention accommodates multiple lengths and French sizes of catheters. A catheter is protected without inhibiting loading or removal of the catheter owing to the nonconfining nature of the device.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

I claim:

1. A catheter packaging device, comprising:
    a base portion including a bottom surface, a perimeter wall, and at least one retaining member extending inward from the perimeter wall; and
    a catheter-holding portion including a protective well and at least one support member, wherein a distal portion of a catheter is suspended within the protective well such that the distal portion does not contact the catheter packaging device when the catheter is held by the at least one support member.

2. The device of claim 1 wherein the shape of the catheter packaging device is ringlike.

3. The device of claim 1 wherein the perimeter wall is oriented perpendicular to the bottom surface of the catheter packaging device.

4. The device of claim 1 wherein the at least one retaining member is positioned to retain a coiled catheter within the catheter packaging device.

5. The device of claim 1 wherein the at least one retaining member comprises a plurality of retaining tabs extending inward from an upper edge of the perimeter wall.

6. The device of claim 1 wherein a recess formed in the bottom surface and perimeter wall of the catheter packaging device provides finger access for ease of removal of a coiled catheter.

7. The device of claim 1 wherein a channel is provided between the perimeter wall and the catheter-holding portion to receive a proximal portion of a catheter.

8. The device of claim 1 wherein the protective well comprises a recessed area sized to suspend a distal portion of a catheter such that the catheter portion does not contact the catheter packaging device.

9. The device of claim 1 wherein the distal portion of a catheter that is suspended within the protective well bears a treated stent.

10. The device of claim 1 wherein the at least one support member comprises a first section extending distally from the protective well and a second section extending proximally from the protective well.

11. The device of claim 10 wherein each section of the support member includes an elongate channel into which a portion of the catheter is placed.

12. The device of claim 11 wherein the channel is arcuate.

13. The device of claim 11 wherein the channel includes a plurality of protrusions extending into the channel from each side to releasably grip a portion of the catheter.

14. The device of claim 1 wherein the device is fabricated using one or more materials selected from a group consisting of polypropylene, polyethylene, a nylon/polyethylene blend, polytetrafluoroethylene (PTFE), and a suitable formable material.

15. The device of claim 1 wherein the device is fabricated using one or more methods selected from a group consisting of blow molding, injection molding, and a suitable molding method.

16. The device of claim 1 wherein the catheter-holding portion is integrally formed into the bottom surface of the catheter packaging device.

17. The device of claim 1 further comprising:
    a luer-holding portion.

18. The device of claim 17 wherein the luer-holding portion includes at least one opening within the perimeter wall positioned to hold one of a wing section or side arm of a luer.

19. A method of protecting a catheter within a catheter packaging device, comprising:
    retaining a first distal portion of the catheter within at least one support member;
    retaining a second distal portion of the catheter within at least one support member;
    suspending a third distal portion of the catheter such that the third distal portion does not contact the catheter packaging device;
    retaining a first proximal portion of the catheter in a coiled configuration within the catheter packaging device; and
    retaining a second proximal portion of the catheter in a fixed position within the catheter packaging device.

20. The method of claim 19 further comprising:
    covering at least a portion of the catheter packaging device.

21. The method of claim 19 wherein the third distal portion of the catheter is between the first and second distal portions of the catheter.

22. The method of claim 19 wherein the third distal portion of the catheter bears a treated stent.

23. The method of claim 19 wherein the first distal portion of the catheter comprises a stylet.

24. The method of claim 19 wherein the second proximal portion of the catheter comprises a luer.

25. The method of claim 19 wherein the first and second distal portions of the catheter are retained by individual sections of the same support member.

26. The method of claim 19 wherein the first and second distal portions of the catheter are retained by individual support members.

27. A system for protecting a catheter within a catheter packaging device, comprising:
    means for retaining a first distal portion of the catheter within at least one support member;
    means for retaining a second distal portion of the catheter within at least one support member;
    means for suspending a third distal portion of the catheter such that the third distal portion does not contact the catheter packaging device;
    means for retaining a first proximal portion of the catheter in a coiled configuration within the catheter packaging device; and
    means for retaining a second proximal portion of the catheter in a fixed position within the catheter packaging device.

28. A catheter packaging device, comprising;
a base portion including a bottom surface, a perimeter wall, and at least one retaining member extending inward from the perimeter wall; and
a catheter-holding portion including a protective well and at least one support member, wherein the at least one support member comprises a first section extending distally from the protective well and a second section extending proximally from the protective well, wherein each section of the support member includes an elongate channel into which a portion of the catheter is placed, and wherein a distal portion of a catheter is suspended within the protective well when the catheter is held by the at least one support member.

29. The device of claim 28 wherein the channel is arcuate.

30. The device of claim 28 wherein the channel includes a plurality of protrusions extending into the channel from each side to releasably grip a portion of the catheter.

31. The device of claim 28 further comprising:
a luer-holding portion.

32. The device of claim 31 wherein the luer-holding portion includes at least one opening within the perimeter wall positioned to hold one of a wing section or side arm of a luer.

33. The device of claim 28 wherein the shape of the catheter packaging device is ringlike.

34. The device of claim 28 wherein the protective well comprises a recessed area sized to suspend a distal portion of a catheter such that the catheter portion does not contact the catheter packaging device.

35. The device of claim 28 wherein the distal portion of the catheter bears a treated stent.

* * * * *